(12) United States Patent
Rhad et al.

(10) Patent No.: US 8,801,742 B2
(45) Date of Patent: Aug. 12, 2014

(54) NEEDLE ASSEMBLY AND BLADE ASSEMBLY FOR BIOPSY DEVICE

(75) Inventors: Edward A. Rhad, Fairfield, OH (US); Andrew P. Nock, Centerville, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 27 days.

(21) Appl. No.: 13/150,950

(22) Filed: Jun. 1, 2011

(65) Prior Publication Data

US 2012/0310110 A1 Dec. 6, 2012

(51) Int. Cl.
*A61B 17/34* (2006.01)

(52) U.S. Cl.
USPC ........... 606/185; 600/562; 600/564; 600/565; 600/566; 600/567

(58) Field of Classification Search
CPC .......... A61B 10/0266; A61B 17/3211; A61B 17/34; A61B 17/3417; A61B 17/3496; A61B 2017/00473
USPC .......................... 600/562, 564, 565, 566, 567
See application file for complete search history.

(56) References Cited

U.S. PATENT DOCUMENTS

| | | | | |
|---|---|---|---|---|
| 5,449,001 | A * | 9/1995 | Terwilliger | 600/567 |
| 5,526,822 | A | 6/1996 | Burbank et al. | |
| 5,607,440 | A * | 3/1997 | Danks et al. | 606/185 |
| 5,609,604 | A * | 3/1997 | Schwemberger et al. | 606/185 |
| 5,685,820 | A * | 11/1997 | Riek et al. | 600/114 |
| 6,086,544 | A | 7/2000 | Hibner et al. | |
| 6,187,022 | B1 * | 2/2001 | Alexander et al. | 606/185 |
| 6,383,145 | B1 * | 5/2002 | Worm et al. | 600/564 |
| 6,544,277 | B1 * | 4/2003 | O'Heeron et al. | 606/185 |
| 6,551,253 | B2 * | 4/2003 | Worm et al. | 600/564 |
| 6,626,849 | B2 | 9/2003 | Huitema et al. | |
| 7,445,739 | B2 * | 11/2008 | Tsonton et al. | 264/154 |
| 7,491,177 | B2 * | 2/2009 | Hibner | 600/566 |
| 7,514,843 | B2 | 4/2009 | Nagahama et al. | |
| 7,854,706 | B2 | 12/2010 | Hibner | |
| 7,895,725 | B2 * | 3/2011 | Beckman et al. | 29/458 |

(Continued)

FOREIGN PATENT DOCUMENTS

WO WO 02/062231 8/2002

OTHER PUBLICATIONS

U.S. Appl. No. 12/843,088, filed Jul. 26, 2010, Mumaw.
U.S. Appl. No. 12/953,715, filed Nov. 24, 2010, Rhad et al.

(Continued)

*Primary Examiner* — Sean Dougherty
(74) *Attorney, Agent, or Firm* — Frost Brown Todd LLC

(57) ABSTRACT

A biopsy device may comprise a probe assembly that has a needle assembly extending distally from the probe assembly. The needle assembly has a needle portion and blade assembly. The blade assembly comprises a blade and a multi-member coupling assembly. The multi-member coupling assembly is configured to couple to the blade and to the needle portion to attach the blade to the needle portion. In one configuration the multi-member coupling assembly comprises two coupling members configure to couple to the blade. The blade may be a flat blade that has a retention channel formed therein, wherein the two coupling members may couple to the blade at the retention channel. The needle portion may comprise a needle and a cutter receiving tube. The needle may be an ovular cross-sectioned tube having a cut-out portion into which a circular cross-sectioned cutter receiving tube may be inserted and coupled thereto.

16 Claims, 12 Drawing Sheets

(56) References Cited

U.S. PATENT DOCUMENTS

| | | | |
|---|---|---|---|
| 8,282,663 B2* | 10/2012 | Smith | 606/190 |
| 8,535,240 B2* | 9/2013 | Flatland et al. | 600/564 |
| 2002/0029007 A1* | 3/2002 | Bryan et al. | 600/565 |
| 2002/0120212 A1 | 8/2002 | Ritchart et al. | |
| 2006/0074345 A1 | 4/2006 | Hibner | |
| 2006/0144548 A1* | 7/2006 | Beckman et al. | 163/1 |
| 2007/0185411 A1 | 8/2007 | Hibner | |
| 2008/0214955 A1 | 9/2008 | Speeg et al. | |
| 2008/0281224 A1 | 11/2008 | Johnson | |
| 2010/0152610 A1 | 6/2010 | Parihar et al. | |
| 2010/0160819 A1 | 6/2010 | Parihar et al. | |
| 2010/0317997 A1 | 12/2010 | Hibner et al. | |
| 2011/0190661 A1* | 8/2011 | Wegener et al. | 600/567 |
| 2011/0245718 A1* | 10/2011 | Flatland et al. | 600/567 |

OTHER PUBLICATIONS

International Search Report and Written Opinion dated Jan. 25, 2013 for Application No. PCT/US2012/037865.

* cited by examiner

NEEDLE ASSEMBLY AND BLADE ASSEMBLY FOR BIOPSY DEVICE

BACKGROUND

Biopsy samples have been obtained in a variety of ways in various medical procedures using a variety of devices. Biopsy devices may be used under stereotactic guidance, ultrasound guidance, MRI guidance, PEM guidance, BSGI guidance, or otherwise. For instance, some biopsy devices may be fully operable by a user using a single hand, and with a single insertion, to capture one or more biopsy samples from a patient. In addition, some biopsy devices may be tethered to a vacuum module and/or control module, such as for communication of fluids (e.g., pressurized air, saline, atmospheric air, vacuum, etc.), for communication of power, and/or for communication of commands and the like. Other biopsy devices may be fully or at least partially operable without being tethered or otherwise connected with another device.

Merely exemplary biopsy devices are disclosed in U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pub. No. 2003/0109803, entitled "MRI Compatible Surgical Biopsy Device," published Jun. 12, 2003; U.S. Pub. No. 2006/0074345, entitled "Biopsy Apparatus and Method," published Apr. 6, 2006; U.S. Pub. No. 2007/0118048, entitled "Remote Thumbwheel for a Surgical Biopsy Device," published May 24, 2007; U.S. Pub. No. 2008/0214955, entitled "Presentation of Biopsy Sample by Biopsy Device," published Sep. 4, 2008; U.S. Pub. No. 2009/0171242, entitled "Clutch and Valving System for Tetherless Biopsy Device," published Jul. 2, 2009; U.S. Pub. No. 2010/0152610, entitled "Hand Actuated Tetherless Biopsy Device with Pistol Grip," published Jun. 17, 2010; U.S. Pub. No. 2010/0160819, entitled "Biopsy Device with Central Thumbwheel," published Jun. 24, 2010; U.S. Pub. No. 2010/0317997, entitled "Tetherless Biopsy Device with Reusable Portion," published Dec. 16, 2010; and U.S. patent application Ser. No. 12/953,715, entitled "Handheld Biopsy Device with Needle Firing," filed Nov. 24, 2010. The disclosure of each of the above-cited U.S. Pat. Nos., U.S. Patent Application Publications, and U.S. Non-Provisional Patent Applications is incorporated by reference herein.

In certain situations it may be preferable for a biopsy device user to have a substantially flat bladed needle to insert into the patient. When using a flat blade, it may preferable to both properly secure the blade to the needle portion and to seal the end of the needle portion. Accomplishing both these preferences may be particularly difficult when combining a flat blade to a very small gauge needle portion.

In addition, some biopsy devices may have a needle portion that has a generally circular cross-section, a generally ovular cross-section, a generally elliptical cross-section, or some other cross-section. In some designs, a shelf or tray has been inserted into an ovular needle portion to create the "figure eight" type of cross-section. However, when mounting the shelf or tray within the ovular cross-sectioned needle portion, the attachment of the tray may be limited by the amount of access permitted to weld the shelf or tray within the needle portion. In addition, the shelf or tray may deform when being inserted or being welded in place. This may result in interference with an internal cutter during the use of a biopsy device.

While several systems and methods have been made and used for obtaining a biopsy sample, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements. In the drawings some components or portions of components are shown in phantom as depicted by broken lines.

Figure 1:
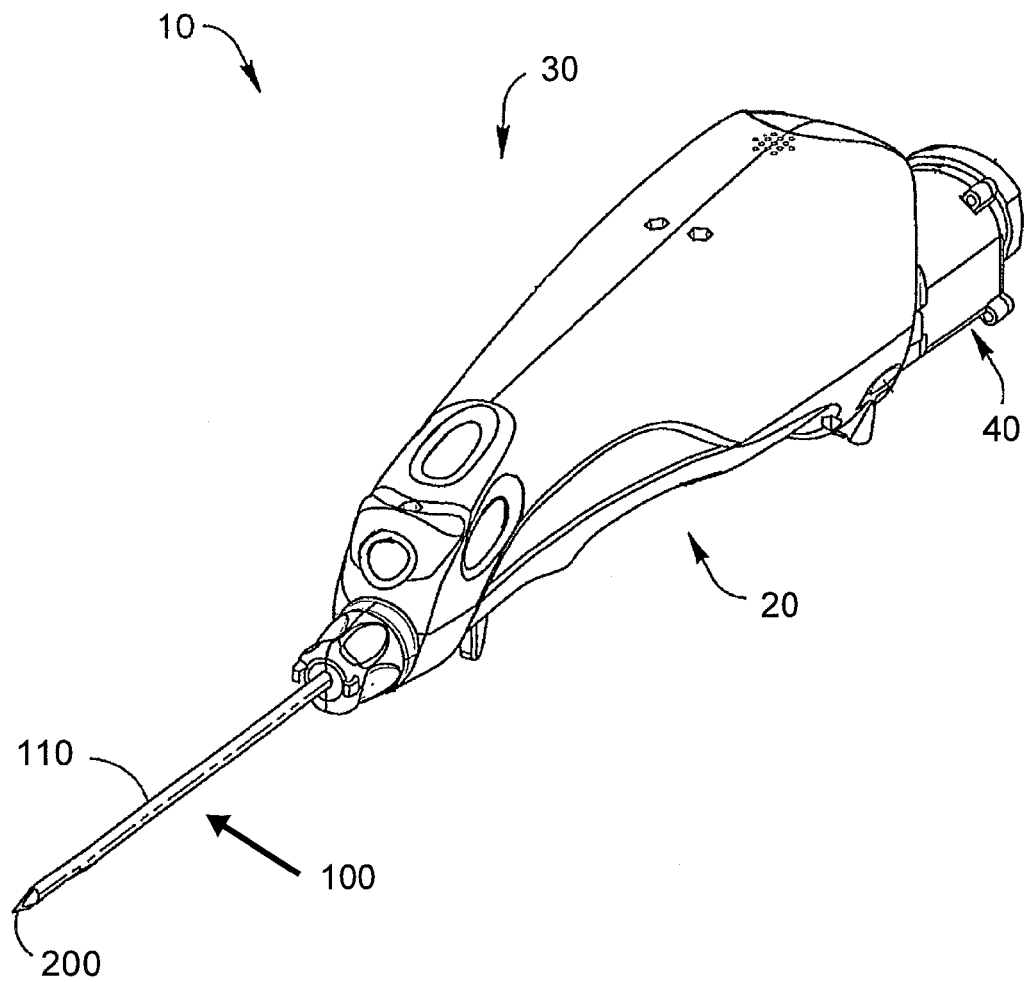
FIG. 1 depicts a perspective view of an exemplary biopsy device showing various components of the exemplary biopsy device.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Overview of Exemplary Biopsy Device

Figure 2:
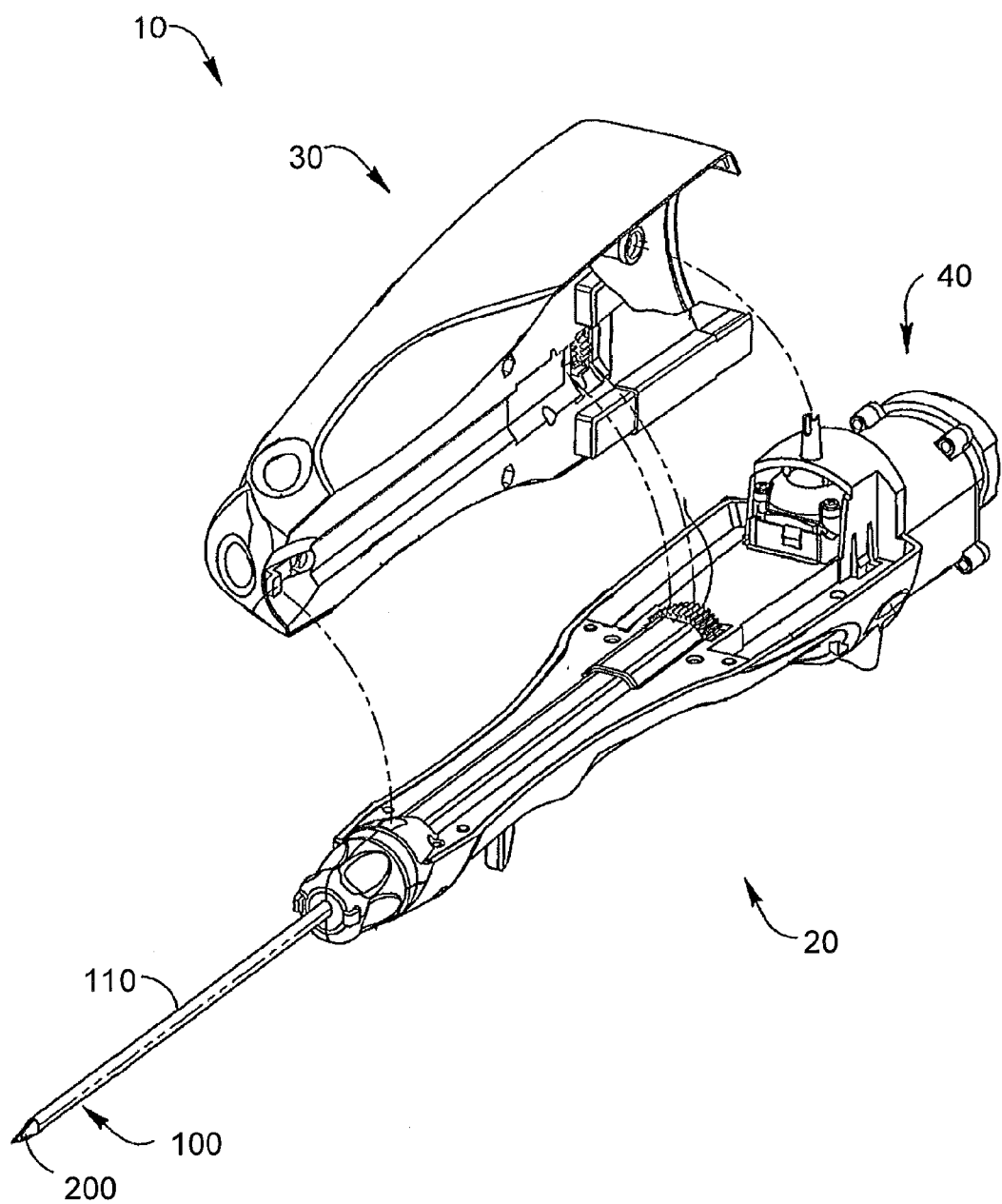
FIG. 2 depicts a perspective view of an exemplary biopsy device showing a holster detached from a probe.

FIG. 1 shows an exemplary biopsy device (10). Biopsy device (10) comprises a probe (20) and a holster (30). Probe (20) comprises a needle assembly (100) that at least partially extends distally from a casing of probe (20) and needle assembly (100) is insertable into a patient's tissue to obtain tissue samples as will be described below. Biopsy device (10) further comprises a tissue sample holder (40) into which the tissue samples are deposited. By way of example only, probe (20) may be a disposable component and holster (30) may be a reusable component to which probe (20) may be coupled, as shown in FIG. 2. Use of the term "holster" herein should not be read as requiring any portion of probe (20) to be inserted into any portion of holster (30). Indeed, in one configuration for biopsy device (10), probe (20) may simply be positioned atop holster (30). Alternatively, a portion of probe (20) may be inserted into holster (30) to secure probe (20) to holster (30). In yet another configuration, a portion of holster (30) may be inserted into probe (20). Further still, probe (20) and holster (30) may be integrally formed as a single unit. In configurations where probe (20) and holster (30) are separable members, a port and/or a seal may be provided on holster (30) to couple with a second port and/or a second seal on probe (20) such that the vacuum produced by a vacuum pump (50) within holster (30) may be fluidly connected to probe (20). Indeed, in one merely exemplary configuration, vacuum pump (50) induces a vacuum within needle assembly (100) as will be described in more detail below. Alternatively, vacuum pump (50) may be independent of holster (30) and probe (20) and may simply be coupled by vacuum tubes to appropriate ports on biopsy device (10). Biopsy device (10) may further be configured in accordance with at least some of the teachings of U.S. patent application Ser. No. 12/953,715, entitled "Handheld Biopsy Device with Needle Firing," filed Nov. 24, 2010, the disclosure of which is incorporated by reference herein. Other suitable structural and functional combinations for probe (20) and holster (30) will be apparent to one of ordinary skill in the art in view of the teachings herein.

II. Exemplary Holster

Figure 3:
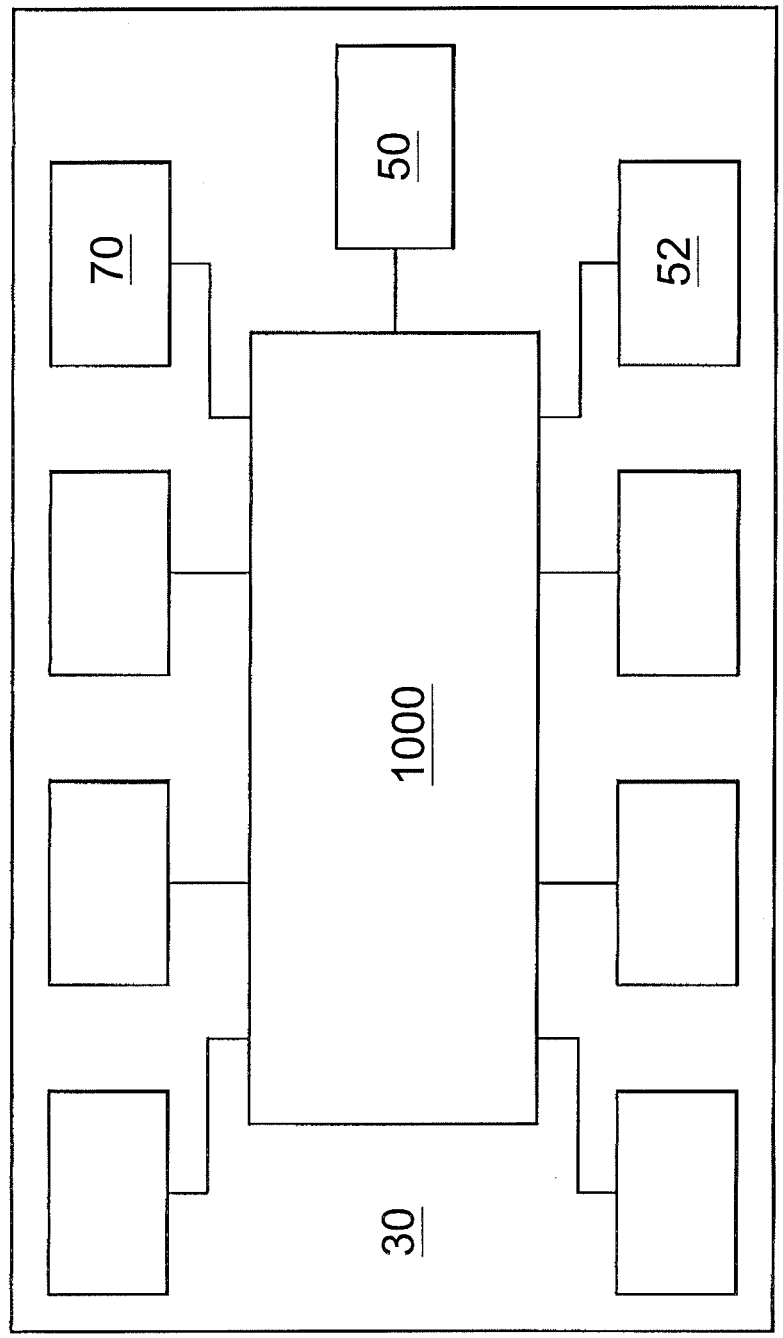
FIG. 3 depicts a schematic view of an exemplary holster showing various electrical and/or electromechanical components contained therein.

Holster (30), shown schematically in FIG. 3, comprises vacuum pump (50), a motor (70), a control module (1000), a vacuum sensor (52), and any other suitable electrical and/or electromechanical components. Vacuum pump (50) of the present example comprises a conventional diaphragm pump that is mechanically coupled to motor (70). Vacuum sensor (52) is coupled to vacuum pump (50) or along any vacuum path therefrom such that vacuum sensor (52) can determine the level of vacuum created by vacuum pump (50). Vacuum sensor (52) is electrically coupled to control module (1000) so that vacuum sensor (52) may output signals indicative of the vacuum level to control module (1000). In the configuration shown, motor (70) is operable to translate and/or rotate a tubular cutter (60), as will be described later herein, and to activate vacuum pump (50), though this is merely optional and a second motor (not shown) may be provided to run vacuum pump (50). Other various configurations for holster (30) may be provided as will be apparent to one of ordinary skill in the art in view of the teachings herein. Indeed, holster (30) may be constructed in accordance with at least some of the teachings of U.S. patent application Ser. No. 12/953,715, entitled "Handheld Biopsy Device with Needle Firing," filed Nov. 24, 2010, the disclosure of which is incorporated by reference herein.

III. Exemplary Needle Assembly

Figure 4:
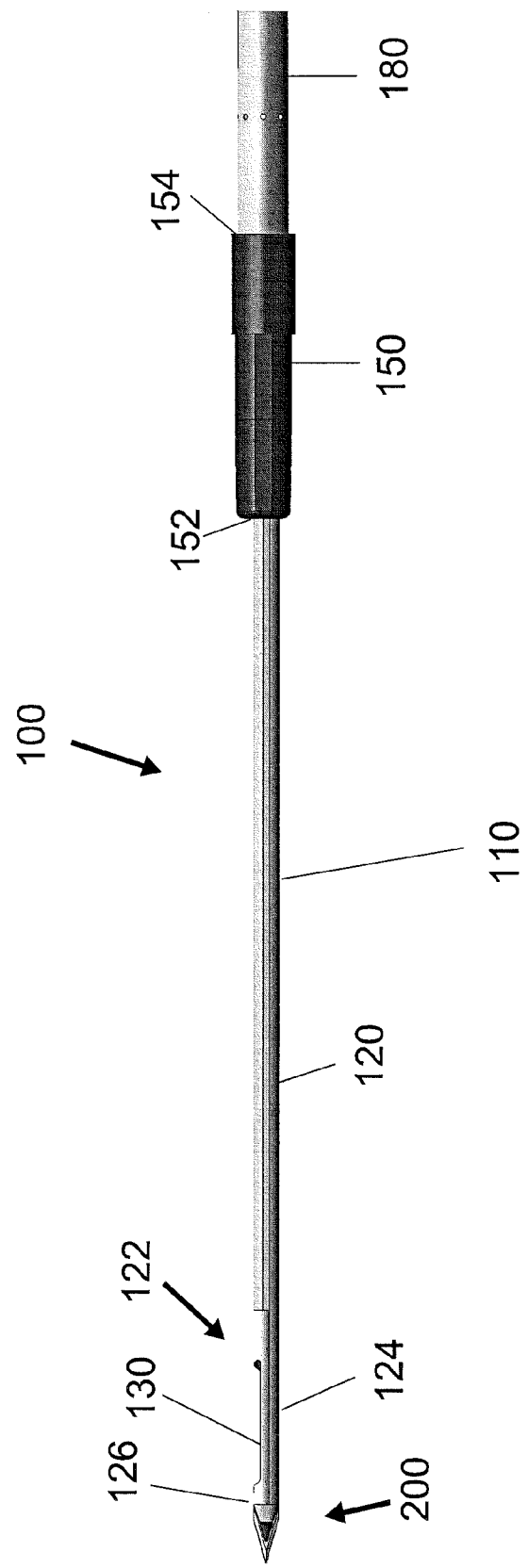
FIG. 4 depicts a side view of an exemplary needle assembly for a biopsy device, the exemplary needle having a blade assembly, a needle portion, a needle coupling member, and a vent sleeve.

FIG. 4 depicts an exemplary needle assembly (100) for use with probe (20).

Needle assembly (100) comprises a needle portion (110), a blade assembly (200), a needle coupling member (150), and a vent sleeve (180). As seen in FIG. 3, needle portion (110) comprises a needle (120) and a cutter receiving tube (130). Needle (120) of the present example is a tube having an ovular cross-section and having a proximal end and a distal end forming a lumen therebetween. It should be understood, however, that needle (120) may have other configurations, such as a circular tube, a square tube, or any other suitable cross-sectional shape for needle (120) as will be apparent to one of ordinary skill in the art in light of the teachings herein. Needle (120) has a cut-out portion (122) extending longitudinally from the distal end of needle (120) and terminating at a position proximal of the distal end. For example, cut-out portion (122) may extend longitudinally along the entire length of needle (120) or cut-out portion (122) may terminate at a longitudinal position distal of the proximal end of needle (120). By way of example only, the longitudinal length of the cut-out portion (122) may be in the range of 0.8 to 4.0 inches. In particular, for a merely exemplary 13 gauge needle, cut-out portion (122) extends longitudinally from the distal end of needle (120) to approximately 1.088 inches proximal of the distal end of needle (120).

Cut-out portion (122) also extends downwardly from the top of needle (120) and terminates at a plane below the top of needle (120). In one merely exemplary configuration, cut-out portion (122) may extend below a mid-point of needle (120). Alternatively, cut-out portion (122) may terminate above the mid-point of needle (120), at the mid-point of needle (120), or at any other suitable point as will be apparent to one of ordinary skill in the art in light of the teachings herein. In the example of a 13 gauge needle, cut-out portion (122) terminates at a plane located approximately 0.08124 inches below the top of needle (120) such that the top most point of cutter receiving tube (130), as will be described in more detail below, is tangentially aligned with the top most point of needle (120) when cutter receiving tube (130) is positioned within cut-out portion (122). Once cut-out portion (122) of needle (120) is removed, a partial needle portion (124) remains and extends distally from the remaining uncut needle (120). Partial needle portion (124) is coupled to cutter receiving tube (130), as will be described in more detail below. Other equally suitable sizes and configurations for cut-out portion (122) and needle (120) will be apparent to one of ordinary skill in the art in view of the teachings herein.

A. Exemplary Cutter Receiving Tube

In some instances, it may be preferable to have two sections in the needle portion of the needle assembly. This may be useful to provide a lateral vacuum to assist in prolapsing tissue through a lateral aperture and/or to provide a vacuum differential on opposite sides of a severed tissue sample to aid the transportation of the tissue sample through the biopsy device. Previously, a pre-formed tray or shelf has been inserted and welded into the needle to create the two sections. However, due to space limitations, the tray may not necessarily be completely welded inside the needle or the tray may deform when inserted. Accordingly, utilizing a tube may eliminate these issues by providing a welding surface on the exterior of the needle and limiting the potential for deformation.

Cutter receiving tube (130) can be sized to be generally coextensive to the length of cut-out portion (122) (e.g., for the 13 gauge needle described above, cutter receiving tube (130) is also approximately 1.088 inches long). Cutter receiving tube (130) is positioned at the location of cut-out portion (122) and fixedly secured to needle (120) and partial needle portion (124). Thus, in combination, cutter receiving tube (130), partial needle portion (124) and needle (120) form needle portion (110). In this configuration, the distal ends of cutter receiving tube (130) and partial needle portion (124) are substantially coplanar and form an attachment end (126) to which blade assembly (200) may be coupled, as will be described in more detail below. In the present example, when cutter receiving tube (130) is aligned within cut-out portion (122), cutter receiving tube (130) is welded to needle (120) and partial needle portion (124), though other suitable attachment methods will be apparent to one of ordinary skill in the art in view of the teachings herein. These may include mechanical attachment (such as by set screws or bolts), adhesive attachment, or any other suitable attachment.

Figure 6:
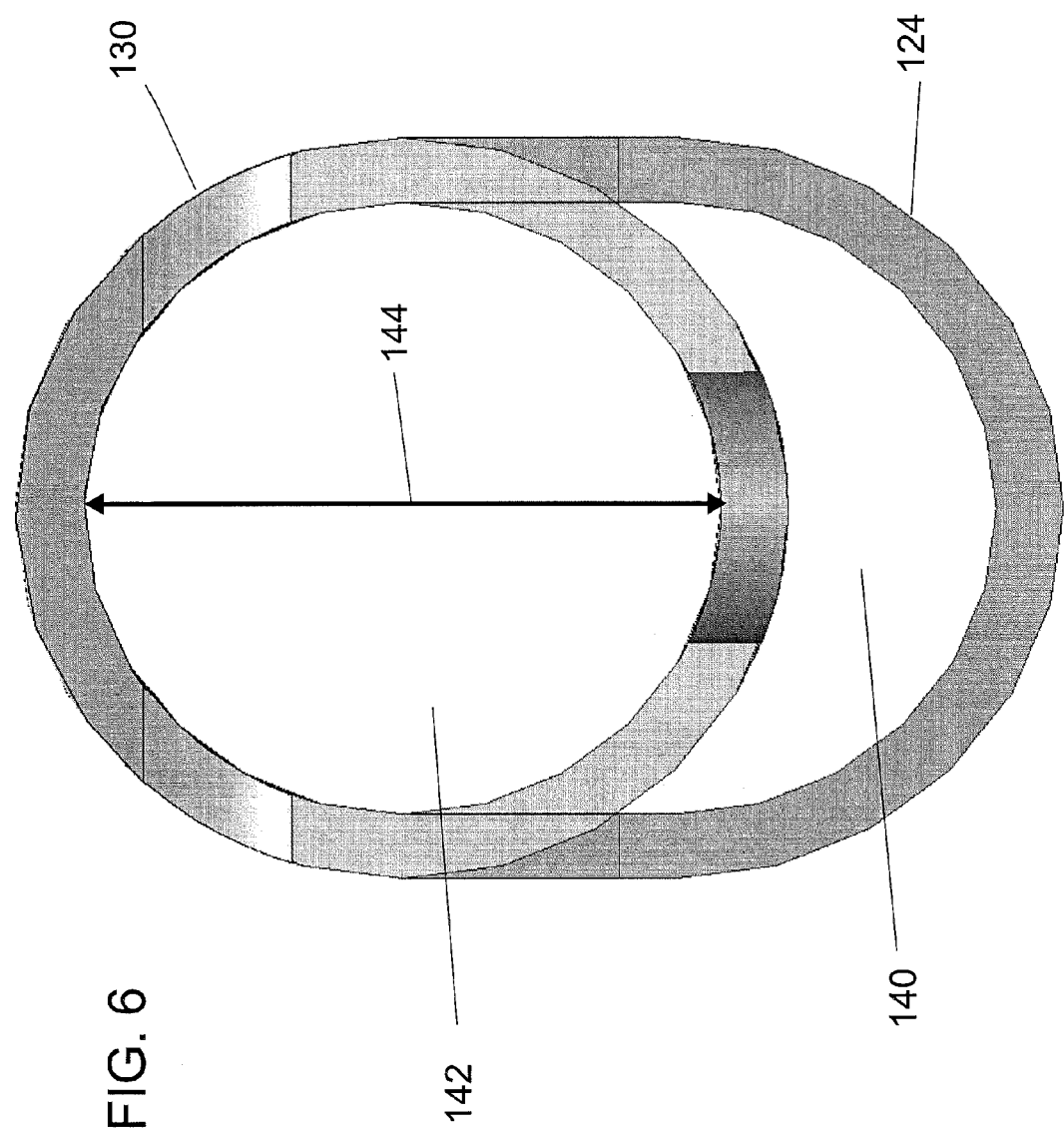
FIG. 6 depicts a front cross-sectional view along line 6-6 of the needle portion of FIG. 5 having a needle and a cutter receiving tube.

Exemplary cutter receiving tube (130) is shown as a tube having a circular cross-section, as best seen in FIG. 6. When cutter receiving tube (130) is secured to partial needle portion (124), the combination of cutter receiving tube (130) and partial needle portion (124) forms a first lumen portion (140) and a second lumen portion (142). Second lumen portion (142) has a circular cross-section having an inner diameter (144) sized such that a tubular cutter (60) having a sharp distal edge may rotate and translate therein. By way of example only, for a 13 gauge needle as discussed above, inner diameter (144) may be approximately 0.086 inches. First lumen portion (140) of the present example has a semi-circular cross-section defined by a lower portion of cutter receiving tube (130) and partial needle portion (124).

Referring back to FIG. 5, cutter receiving tube (130) further comprises a lateral aperture (132) and a plurality of openings (134). Lateral aperture (132) is sized to receive prolapsed tissue during operation of biopsy device (10). The plurality of openings (134) in cutter receiving tube (130) are formed in the sidewall opposite to lateral aperture (132) such that the plurality of openings (134) provide fluid communication between first lumen portion (140) and second lumen portion (142). For instance, first lumen portion (140) may selectively provide atmospheric air to vent second lumen portion (142), first lumen portion (140) may selectively provide a vacuum to second lumen portion (142) to prolapse the tissue into lateral aperture (134), and/or first lumen portion (140) may provide saline to flush first lumen portion (140), second lumen portion (142), and/or tubular cutter (60) during operation of biopsy device (10), as will be described in greater detail below.

Figure 5:
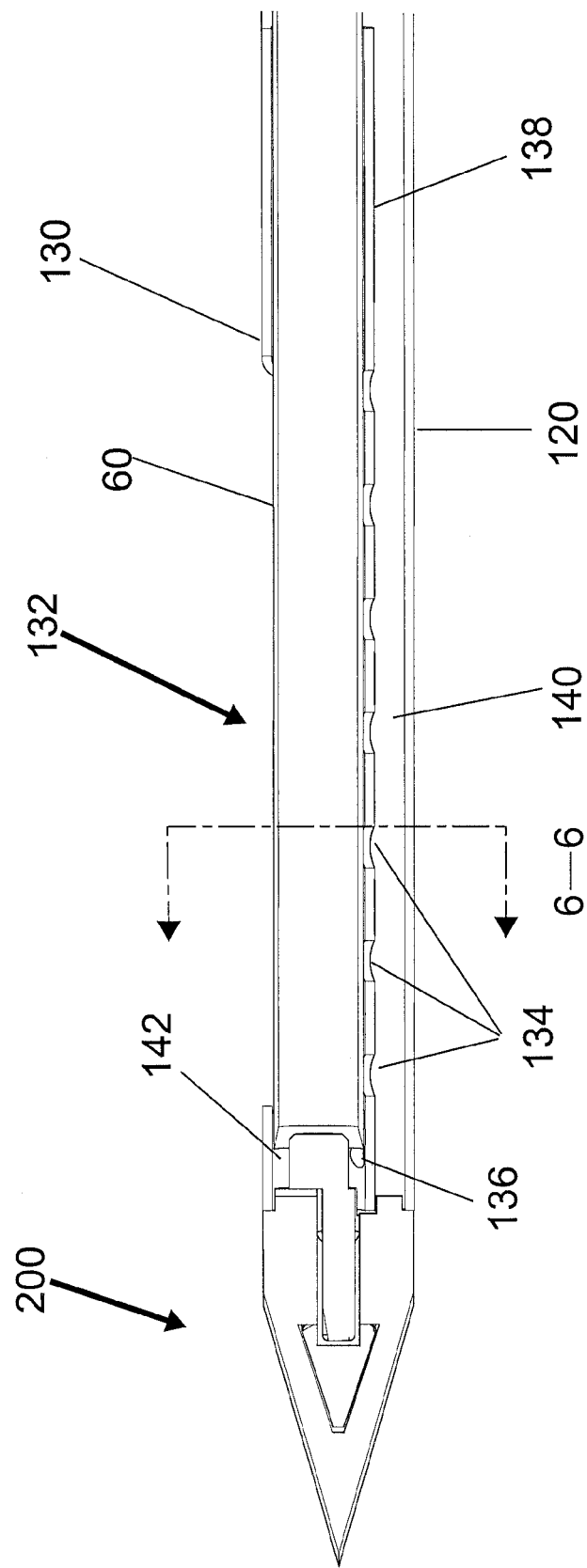
FIG. 5 depicts a cross-sectional side view of the tip of the exemplary needle assembly of FIG. 4 showing the blade assembly, the needle portion, and a tubular cutter in a proximal-most position.

As shown in FIG. 5, the plurality of openings (134) comprise circular openings, though it should be understood that the plurality of openings (134) may have any other configuration, including ovular openings, slots, scallops, triangular openings, a mesh grid, or any other suitable configuration. Cutter receiving tube (130) also has a foremost opening (136) formed distally of the plurality of openings (134) and just proximal of the distal end of cutter receiving tube (130). Foremost opening (136) is further aligned to be distal of the distal edge of lateral aperture (132) such that the distal end of the prolapsed tissue is also drawn towards foremost opening (136) when a vacuum is applied. In addition, second lumen portion (142) may remain in fluid communication with first lumen portion (140) through foremost opening (136) even when tubular cutter (60) is advanced to a position where the sharp distal edge is located at a longitudinal position that is distal to the longitudinal position of the distal edge of lateral aperture (132).

Cutter receiving tube (130) of the present example further comprises a tubular cutter dwelling portion (138). Dwelling portion (138) is located proximal to the proximal edge of lateral aperture (132) such that the tubular cutter (60) may be retracted into dwelling portion (138) between cuts of prolapsed tissue during operation of biopsy device (10). In the case of a merely exemplary 13 gauge needle, dwelling portion (138) extends longitudinally approximately 0.273 inches from the proximal edge of lateral aperture (132). A guide portion (not shown) may also be provided, which extends proximally from dwelling portion (138) of cutter receiving tube (130). Guide portion may be configured to be a simple tab extending from the proximal end of cutter receiving tube (130) on the sidewall opposite lateral aperture (132). Guide portion may further be bent downwardly towards the sidewall of needle (120) that is opposite to lateral aperture (132) such that when tubular cutter (60) is inserted into the proximal end of needle (120), guide portion provides a funnel like function to guide tubular cutter (60) into cutter receiving tube (130). Guide portion may further comprise a plurality of openings to permit fluid communication through guide portion and into first lumen portion (140) as described above. Of course, as with any other component described herein, any other suitable configuration for cutter receiving tube (130) may be used.

B. Exemplary Blade Assembly

Utilizing a substantially flat blade may be preferable in certain situations to reduce the impact of inserting a biopsy needle in a patient. However, for very small needles, it may be difficult to properly couple a small, flat blade to the needle. In some instances a plastic molding may be formed around the blade, through a hole in the blade, and coupled to the needle. However, the attachment to the needle may be limited due to the coupling of plastic to a metal needle. Providing a metal to metal contact region between the blade assembly and the needle may permit the blade assembly to be welded to the needle, thereby providing a stronger bond between the blade assembly and the needle.

1. Exemplary Blade

Figure 7:
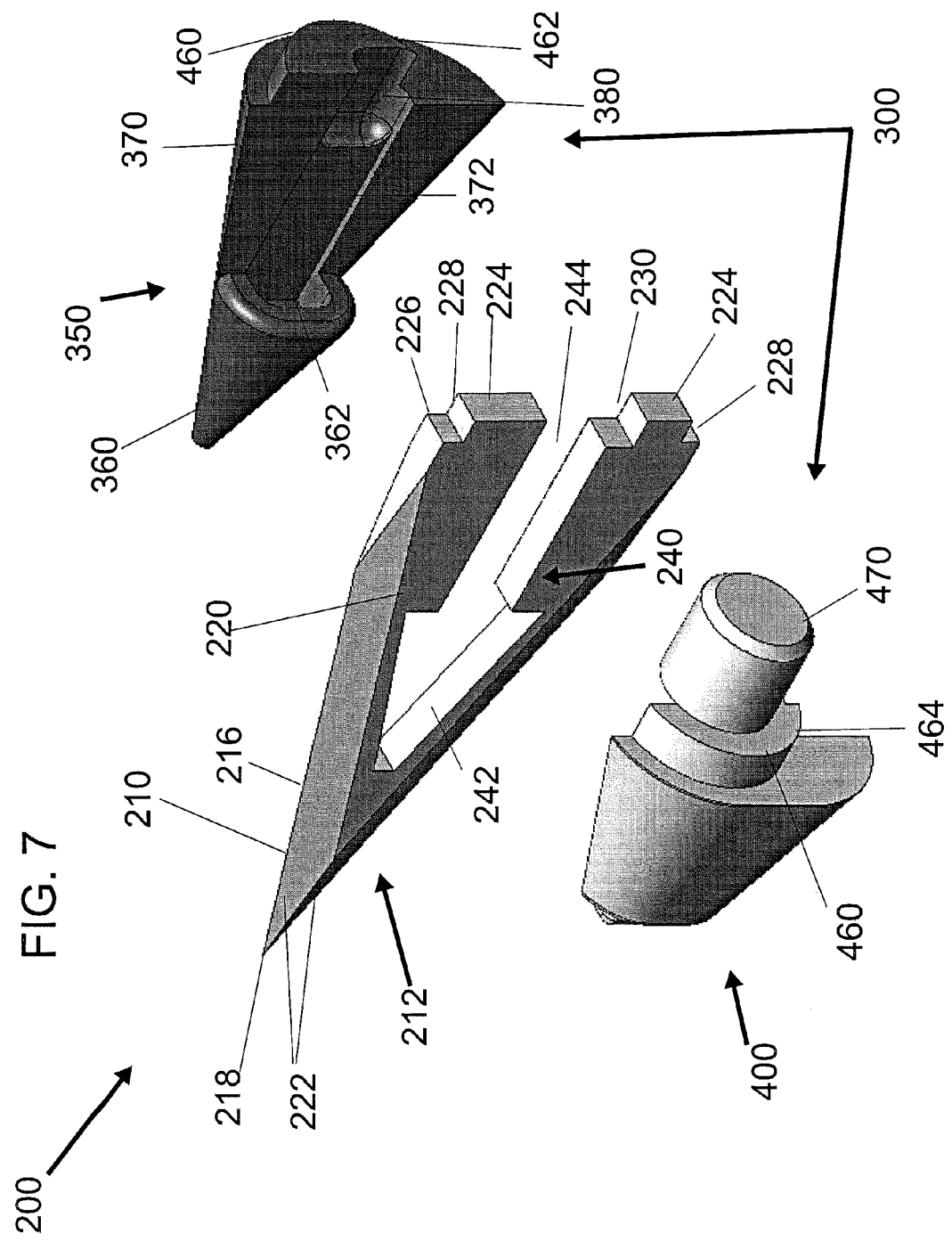
FIG. 7 depicts an exploded isometric view of the blade assembly of FIG. 5 having a first coupling member, a second coupling member, and a blade.
Figure 8:
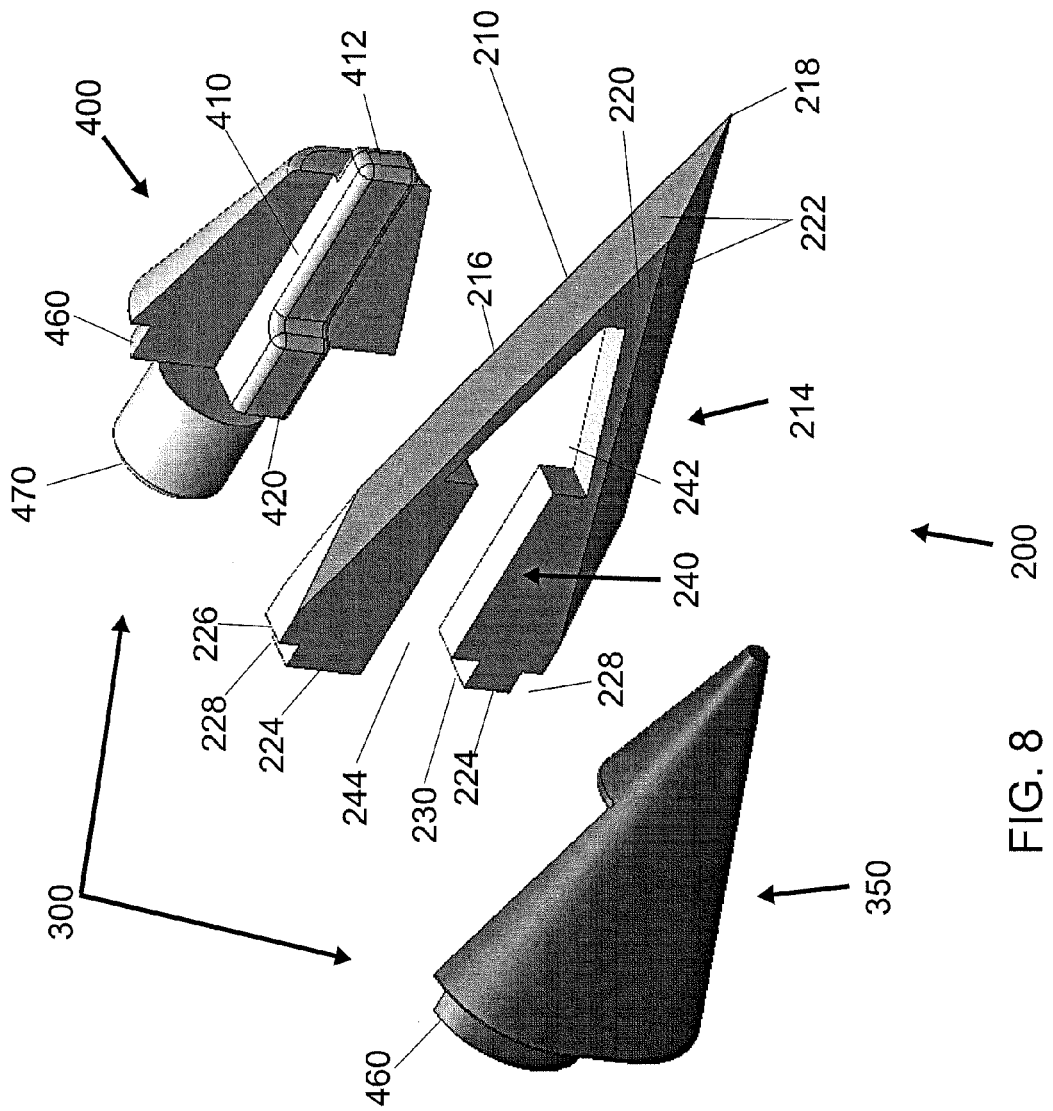
FIG. 8 depicts an alternative exploded isometric view of the blade assembly of FIG. 7.

As seen in FIGS. 5, and 7-8, needle assembly (100) further comprises a blade assembly (200) located at the distal end of needle assembly (100) and coupled to the distal end of needle portion (110). Blade assembly (200) comprises a blade (210) and a multi-member coupling assembly (300). Blade (210) is shown in FIGS. 7-8 as a generally flat blade having a first side (212) (shown in FIG. 7) and a second side (214) (shown in FIG. 8). First side (212) comprises a planar portion (220) and a pair of sharpened leading edges (216) that intersect at a tip (218) at a distal end of blade (210). Leading edges (216) and tip (218) are coplanar within a plane that is parallel to planar portion (220). A pair of honed facets (222) extend from leading edges (216) to planar portion (220), as shown in FIGS. 7-8. Second side (214) is substantially identical in construction to first side (212), though it should be understood that blade (210) may also be asymmetrical, with second side (214) comprising only a flat planar portion or being configured differently from first side (212). Blade (210) may be further configured in accordance with at least some of the teachings of U.S. Pat. Pub. No. 2008/0281224, entitled "Biopsy Device Needle Tip," published Nov. 13, 2008, the disclosure of which is incorporated by reference herein.

At a proximal end of blade (210), a pair of tangs (224) extend proximally from a generally planar proximal surface (226) of blade (210). A pair of outer notches (228) are sized and configured to correspond to the sidewall thicknesses of cutter receiving tube (130) and partial needle portion (124) to allow blade (210) to be partially inserted into attachment end (126) using notches (228), as seen in FIG. 5. An inner notch (230) is located just above the lower tang (224) and is sized and configured to correspond to the sidewall thickness of the portion of cutter receiving tube (130) having the plurality of openings (134), though it should be understood that inner notch (230) is merely optional. As seen in FIG. 5, tangs (224) of the present example are not symmetrical due to inner notch (230) and the asymmetry of needle portion (110). In one alternative configuration, tangs (224) may be symmetrical. In the present example, the combination of tangs (224), outer notches (228), and inner notch (230) synergistically cooperate to limit the vertical movement of blade (210) when coupled to attachment end (126) of needle portion (110).

A retention channel (240) is formed in blade (210), as shown in FIGS. 7-8. By way of example only, retention channel (240) is an arrow-shaped cut-out having a first region (242) and a second region (244). First region (242) is a substantially triangular region (e.g., the head of an arrow) and second region (244) is a substantially rectangular region (e.g., the body of an arrow). In the present configuration, second region (244) is sized to be narrower than the proximal end of first region (242), though this is merely optional. In one alternative, first region (242) and/or second region (244) may be a circular region, a rectangular region, or any other suitably shaped region. In addition, retention channel (240) may not be a single continuous cut-out portion, but may instead comprise multiple openings formed through blade (210). For example, retention channel (240) may comprise two independent circular through-holes formed through blade (210). The circular through-holes may be longitudinally aligned, vertically aligned, or in any other suitable arrangement. It should be understood that retention channel (240) may be configured in variety of other suitable manners as will be apparent to one of ordinary skill in view of the teachings herein.

2. Exemplary Multi-Member Coupling Assembly

In exemplary blade assembly (200) shown in FIGS. 7-8, blade (210) is held in place by multi-member coupling assembly (300). Exemplary multi-member coupling assembly (300) is shown as a two piece assembly comprising a first coupling member (350) and a second coupling member (400), though it should be understood that multi-member coupling assembly (300) is not limited to two members. Indeed, multi-member coupling assembly (300) may have any number of members including one-, three-, four-, or five-piece assemblies, or any other assembly as will be apparent to one of ordinary skill in the art in light of the teachings herein. In the present example, when first coupling member (350) and second coupling member (400) are coupled, blade (210) is substantially restrained by the resulting multi-member coupling assembly (300). As shown in FIGS. 7-8, the combination of first coupling member (350) and second coupling member (400) forms a substantially conical member having a gap through which a bridge member (410), corresponding to second region (244) of retention channel (240), connects first coupling member (350) to second coupling member (400). Thus, when first coupling member (350) and second coupling member (400) are coupled together with blade (210) therebetween, blade (210) is substantially restrained by the resulting multi-member coupling assembly (300) interlocking with retention channel (240).

A receiving tube mount (460) longitudinally extends from the proximal surface of multi-member coupling assembly (300) such that receiving tube mount (460) is insertable into a portion of cutter receiving tube (130). In the present example, receiving tube mount (460) is sized to substantially conform to inner diameter (144) of cutter receiving tube (130). Accordingly, when receiving tube mount (460) is inserted into cutter receiving tube (130), receiving tube mount (460) is substantially restrained therein. Receiving tube mount (460) of the present example is a cylindrical protrusion extending from multi-member coupling assembly (300) and insertable into the circular cutter receiving tube (130). In the present example, receiving tube mount (460) is divided into two sections (462, 464), each of which corresponds to either first coupling member (350) or second coupling member (400), though it should be understood this is merely optional. Indeed, receiving tube mount (460) may be formed entirely on either first coupling member (350) or second coupling member (400) in a similar fashion as tissue plug (470), as will be described in more detail below. Alternatively, in other multi-member coupling assemblies, receiving tube mount may be divided into more than two sections on the plurality of members of the alternative multi-member coupling assemblies.

In the present example, a tissue plug (470) extends proximally from receiving tube mount (460), though it should be understood that if receiving tube mount (460) is not provided, tissue plug (470) may simply extend proximally from the proximal surface of multi-member coupling assembly (300). Tissue plug (470) is configured such that when tubular cutter (60) is advanced to sever the prolapsed tissue, tubular cutter (60) can advance past tissue plug (470) at or near the end of the cutting stroke. Accordingly, when tubular cutter (60) is advanced to sever the prolapsed tissue, tissue plug (470) abuts the distal end of the prolapsed tissue to provide a surface against which the tissue is held in place. As shown in FIGS. 7-8, tissue plug (470) is a cylindrical member that is sized to fit within the inner diameter of tubular cutter (60), though it should be understood that tissue plug (470) may be other geometric shapes, including a cube, a cuboid, a half egg-shaped member, a hemi-spherical member, a hemi-ovular member, or any other suitable configuration as will be apparent to one of ordinary skill in the art in view of the teachings herein. When tubular cutter (60) is advanced against the prolapsed tissue, tissue plug (470) of the present example prevents the tissue from merely being pushed by tubular cutter (60) and instead assists in severing the tissue. Tubular cutter (60) may be advanced beyond the proximal end of the tissue plug (470) to substantially ensure that the prolapsed tissue is severed.

As described above, multi-member coupling assembly (300) of the present example comprises first coupling member (350) and second coupling member (400), the combination of which is a substantially conical member having a bridge member (410) therebetween. As shown in FIGS. 7-8, first coupling member (350) is a semi-conical member having a first portion (360) and a second portion (370). First portion (360) is sized and configured to be insertable through first region (242) in blade (210). By way of example only, first portion (360) is a conically shaped portion that is sized to have a cross-sectional portion that substantially corresponds to the shape of first region (242). Alternatively, if first region (242) is designed to have an alternative shape, such as a circular shape, a rectangular shape, or any other shape, then the cross-sectional portion of first portion (360) would have a similar shape as well. When first portion (360) is inserted into first region (242) of retention channel (240), the proximal end of first portion (360) substantially retains blade (210) in the longitudinal direction. In the present configuration, first portion (360) is a three-dimensional conical member having a width (362) that is wider than a blade width (250) of blade (210). First portion (360) further comprises a head recess (362) into which a portion of second coupling member (400) may be inserted, as will be described below.

Second portion (370) of first coupling member (350) is shown as half of the lower portion of a conical member. Second portion (370) of the present example has a corresponding half formed by second coupling member (400) such that the combination form a substantially conically shaped portion, though it should be understood that this configuration is merely optional. As seen in FIGS. 7-8, second portion (370) has a flat inner surface and a rounded outer surface. In the present example, second portion (370) further has a bridge recess (372) formed within the flat inner surface into which a portion of bridge member (410) of second coupling member (400) may be inserted.

First coupling member (350) further comprises a section (462) of receiving tube mount (460) that extends longitudinally from second portion (370), as shown in FIGS. 7-8. First coupling member (350) also has a rear alignment recess (380) that is formed at least partially in section (462). Rear alignment recess (380) is configured to receive a rear alignment member (420) of second coupling member (400) to better ensure alignment and proper assembly of multi-member coupling assembly (300), though it should be understood that this is merely optional. Of course, as with any other component described herein, any other suitable configuration for first coupling member (350) may be used.

Second coupling member (400) is configured to couple with first coupling member (350) to collectively form multi-member coupling assembly (300). In the present example, second coupling member (400) is a complementary semi-conical member to second portion (370) of first coupling member (350). Second coupling member (400) further comprises a bridge member (410) and a distal protrusion (412). Distal protrusion (412) is sized to be insertable into head recess (362), and bridge member (410) is sized to be at least partially insertable into bridge recess (372) of first coupling member (350), as seen in FIGS. 7-8. Thus, when second coupling member (400) is coupled to first coupling member (350), a substantially conical member is formed having a bridge portion connecting the two lower portions. Second coupling member (400) also has a complementary section (464) of receiving tube mount (460) that extends proximally from the proximal end of second coupling member (400). When second coupling member (400) and first coupling member (350) are coupled, the two sections (462, 464) align to form receiving tube mount (460). As discussed above, second coupling member may further comprise a rear alignment member (420) sized and configured to be insertable into rear alignment recess (380) to better ensure alignment of second coupling member (400) with first coupling member (350). In the present example, a tissue plug (470) extends from a proximal surface of section (464), though, as noted above, tissue plug (470) may be divided into various sections for each of the members of the multi-member coupling assembly (300). Of course, as with any other component described herein, any other suitable configuration for second coupling member (400) may be used.

To assemble blade assembly (200) of the present example, initially first portion (360) of first coupling member (350) is inserted through first region (242) of retention channel (240). First coupling member (350) of the present example is aligned such that the flat inner surface of second portion (370) is parallel and adjacent to planar portion (220) of second side (214) of blade (210). As a result, bridge recess (372) is substantially aligned with second region (244) of retention channel (240). Distal protrusion (412) of second coupling member (400) is then inserted into head recess (362) of first portion (360) of first coupling member (350) and bridge member (410) of second coupling member (400) is inserted into bridge recess (372) of second portion (370) of first coupling member (350). Thus, when second coupling member (400) and first coupling member (350) are assembled about blade (210), the combination of retention channel (240), distal protrusion (412), head recess (362), bridge member (410) and bridge recess (372) cooperatively retain blade (210) between first coupling member (350) and second coupling member (400). In the present example, this synergistic coupling is accomplished via "sandwiching" blade (210) between first coupling member (350) and second coupling member (400), though it should be understood that the coupling may be accomplished in a variety of alternative ways as will be apparent to one of ordinary skill in the art in view of the teachings herein.

For instance, a first coupling member (350) may alternatively be insertable only through first region (242) and extend outwardly from both first side (212) and second side (214) of blade (210). First coupling member (350) may include retaining features, such as head recesses (362), into which a portion of a second coupling member (400) may be coupled. A second coupling member (400) may be insertable only through second region (244) and extend outwardly from both first side (212) and second side (214) of blade (210). Accordingly, when second coupling member (400) and first coupling member (350) are longitudinally coupled together in this configuration, blade (210) is not necessarily "sandwiched" between first coupling member (350) and second coupling member (400); rather, first coupling member (350) and second coupling member (400) merely retain blade (210) as a result of their positioning within retention channel (240). As with other components, various other combinations for first coupling member (350) and second coupling member (400) will be apparent to one of ordinary skill in the art in view of the teachings herein. Moreover, multi-member coupling assembly (300) is not limited to two coupling members; instead, multi-member coupling assembly (300) may comprise more than two coupling members or, multi-member coupling assembly (300) may comprise a single member.

In the present example, with multi-member coupling assembly (300) assembled with blade (210) therebetween, the resulting combination has blade (210) extending distally and receiving tube mount (460) and tissue plug (470) extending proximally. Utilizing receiving tube mount (460) extending proximally from multi-member coupling assembly (300), blade assembly (200) may be coupled to needle portion (110). In the present configuration, receiving tube mount (460) is sized to be insertable into cutter receiving tube (130), as best seen in FIG. 5. In one configuration, receiving tube mount (460) may be sized such that a frictional fit attachment occurs when receiving tube mount (460) is inserted into cutter receiving tube (130). Alternatively, receiving tube mount (460) may be slightly smaller than inner diameter (144) of cutter receiving tube (130) such that receiving tube mount (460) may be more easily inserted therein when blade (210) is present. Blade assembly (200) may be further secured to needle portion (110) by welding, by adhesive attachment, by mechanical attachment (such as inset screws or bolts), or by any other suitable method as will be apparent to one of ordinary skill in light of the teachings herein.

C. Exemplary Needle Coupling Member

Figure 9:
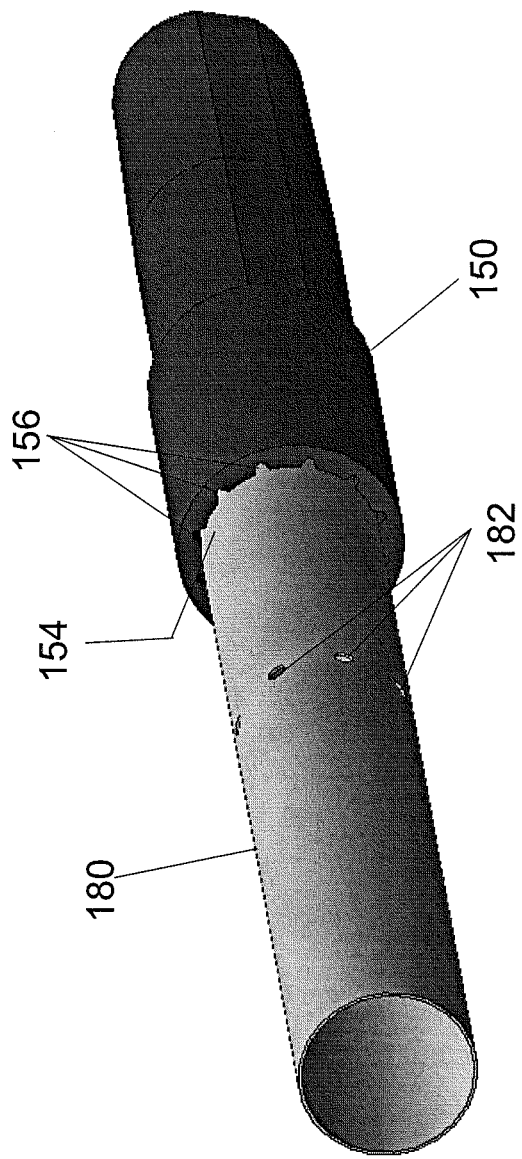
FIG. 9 depicts a rear perspective view of the needle coupling member and the vent sleeve of the needle of FIG. 4.

Referring back to FIG. 4, needle coupling member (150) is coupled to the proximal end of needle portion (110) and to a distal end of vent sleeve (180). In the present example, needle coupling member (150) is a plastic member configured to couple needle portion (110) to vent sleeve (180), though it should be understood that needle coupling member (150) may be made of any suitable material, including metal, rubber, synthetic materials, or any other suitable material. Needle coupling member (150) comprises a needle recess (152) formed in the distal end and a vent sleeve recess (154) formed in the proximal end. As shown in FIG. 9, vent sleeve recess (154) is sized to receive a portion of a distal end of vent sleeve (180), as will be described in more detail below. In the present example, vent sleeve recess (154) is a cylindrical recess corresponding to the cross-sectional shape of vent sleeve (180). Vent sleeve recess (154) may be sized such that a frictional fit attachment occurs when vent sleeve (180) is inserted therein. A plurality of adhesive bores (156) are formed in needle coupling member (150) and are radially disposed about vent sleeve recess (154). Adhesive bores (156) of the present example extend from the proximal surface of needle coupling member (150) to the distal end of vent sleeve recess (154), though it should be understood that adhesive bores (156) may extend distally from the proximal surface of needle coupling member (150) such that adhesive bores (156) do not terminate at the distal end of vent sleeve recess (154). Accordingly, when vent sleeve (180) is inserted into vent sleeve recess (154), an adhesive, such as an epoxy, may be injected into adhesive bores (156) to further secure vent sleeve (180) to needle coupling member (150).

Needle recess (152) is substantially similar to vent sleeve recess (154), except needle recess (152) is formed in the distal end of needle coupling member (150) and is sized to receive a portion of the proximal end of needle portion (110). In the present configuration for needle portion (110) having an ovular needle (120), needle recess (152) is an ovular shaped recess. A plurality of adhesive bores (156) are formed in needle coupling member (150) that are radially disposed about needle recess (152) in a similar manner to adhesive bores (156) encircling vent sleeve recess (154). Accordingly, when needle portion (110) is inserted into needle recess (152), an adhesive, such as an epoxy, may be injected into adhesive bores (156) to further secure needle portion (110) to needle coupling member (150). Other suitable configurations for needle coupling member (150) will be apparent to those of ordinary skill in the art in view of the teachings herein.

D. Exemplary Vent Sleeve

As described above, vent sleeve (180) is coupled to the proximal end of needle coupling member (150) and extends proximally therefrom. A shuttle valve slider may be disposed within vent sleeve (180), such as the shuttle valve slider as described in U.S. patent application Ser. No. 12/953,715, entitled "Handheld Biopsy Device with Needle Firing," filed Nov. 24, 2010, the disclosure of which is incorporated by reference herein. A distal portion of vent sleeve (180) is insertable within the proximal end of needle coupling member (150). As described above, the outer diameter of vent sleeve (180) and vent sleeve recess (154) of needle coupling member (150) are secured together in the present example such that vent sleeve (180) and needle coupling member (150) rotate and/or translate unitarily. It should also be understood that, even with tubular cutter (60) disposed through vent sleeve (180) and needle coupling member (150), the interior of vent sleeve (180) is in fluid communication with second lumen portion (142) of needle portion (110) via an ovular opening through needle coupling member (150). Vent sleeve (180) includes a plurality of transverse openings (182) that are longitudinally co-located with each other and that are equidistantly spaced from each other about the outer perimeter of vent sleeve (180) at their common longitudinal position. Transverse openings (182) provide communication of atmospheric air to the interior of vent sleeve (180) such that when a shuttle valve slider is in a predetermined position, atmospheric air can be fluidly communicated to second lumen portion (142) as desired.

Accordingly, with blade assembly (200) coupled to needle portion (110), needle portion (110) coupled to needle coupling member (150), and needle coupling member (150) coupled to vent sleeve (180), needle assembly (100) is thus formed and may be incorporated into probe (20) for use with biopsy device (10). As will be readily apparent to those of ordinary skill in the art in view of the teachings herein, vent sleeve (180) and/or needle coupling member (150) may be substituted with alternative components or even omitted entirely from needle assembly (100).

III. Exemplary Tip Protector

Figure 10:
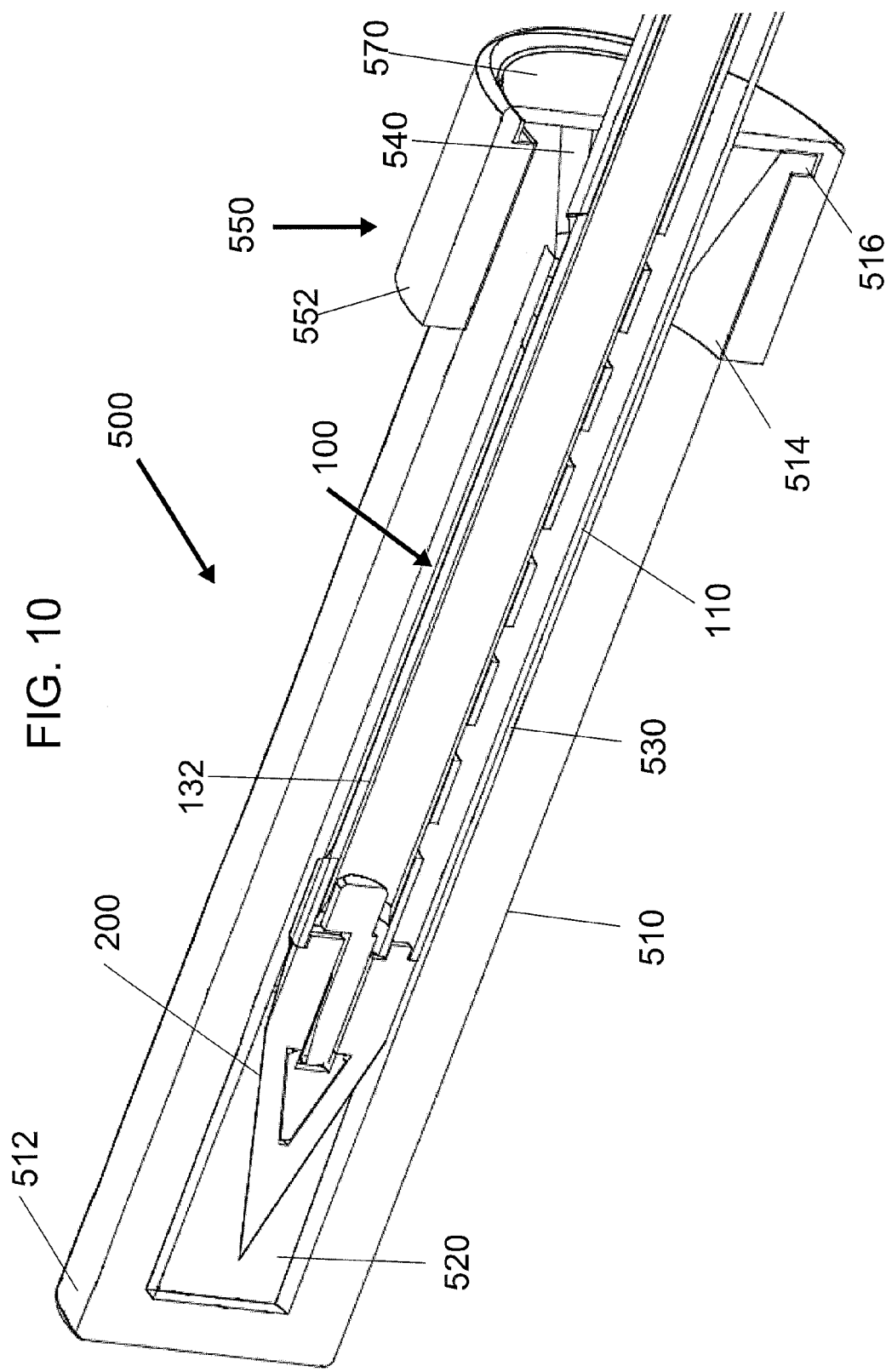
FIG. 10 depicts a perspective side cross-sectional view of an exemplary needle tip protector.

FIG. 10 shows an exemplary needle tip protector (500) for use with exemplary needle assembly (100). In this example, needle tip protector (500) comprises a body (510) and a seal (550). In some versions, body (510) is comprised of polycarbonate; however other suitable materials will be apparent to those of ordinary skill in the art in view of the teachings herein. Body (510) comprises a distal portion having a closed distal end (512) and proximal portion having an open proximal end (514). Proximal end (514) comprises an outwardly extending annular flange (516). In some versions, body (510) is configured to cover only enough of needle assembly (100) such that lateral aperture (132) is contained within body (510). Of course, body (510) may be configured to cover more or less of needle assembly (100) as will be apparent to one of ordinary skill in the art in view of the teachings herein. In the present example, the polycarbonate of body (510) is translucent (such as in a tinted polycarbonate body) such that a user may see through body (510) to inspect blade assembly (200) prior to use. It should be understood, though, that body (510) may be clear or opaque and/or have any suitable combination of such properties.

In the present example, body (510) comprises a blade recess (520), a lateral aperture recess (530), and a funnel (540). As shown in FIG. 10, funnel (540) extends distally from proximal end (514) of body (510) and funnel (540) is configured to aid the insertion of needle portion (110) and blade assembly (200) into body (510), though it should be understood that funnel (540) is merely optional. Lateral aperture recess (530) of the present example extends distally from funnel (540) and is sized to receive a part of needle portion (110) therein. In the present configuration, lateral aperture recess (530) has an ovular cross-section corresponding to needle portion (110), though it should be understood that lateral aperture recess (530) may have any other suitable cross-sectional geometry. Moreover, lateral aperture recess (530) may have a cross-section that is larger than needle portion (110) such that a fluid, for example saline or atmospheric air, may be contained therein. Blade recess (520) extends distally from the proximal end of lateral aperture recess (530) and is sized to receive a blade, such as blade assembly (200) described above. The present blade recess (520) is shown as a rectangular recess that is narrower than lateral aperture recess (530), although, alternatively, blade recess (520) may be a conical recess that substantially conforms to the tapered blade of blade assembly (200). Further still, blade recess (520) may not be narrower than lateral aperture recess (530); instead, blade recess (520) may be the same size as lateral aperture recess (530) or may even be larger than lateral aperture recess (530). Collectively, blade recess (520) and lateral aperture recess (530) have a longitudinal depth such that lateral aperture (132) of needle portion (110) is located distally of proximal end (514) when blade assembly (200) and needle portion (110) of needle assembly (100) are inserted therein.

Seal (550) is coupled to proximal end (514) of body (510). Seal (550) may comprise a variety of materials, including rubber, nitrile rubber, polychloroprene, silicone rubber, or any other suitable elastomeric or resilient material. Seal (550)

comprises an attachment portion (552) and a sealing portion (570). Attachment portion (552) is sized and configured to fit onto body (510) at proximal end (514) such that a seal is formed between attachment portion (552) and the exterior of body (510). In the present example, since body (510) has a circular cross-sectional shape at proximal end (514), attachment portion (552) will have a circular profile as well. Attachment portion (552) of the present configuration is a hollow cylindrical member extending distally from sealing portion (570). In one merely exemplary configuration, attachment portion (552) has an outer diameter that is slightly smaller than the diameter of body (510) such that when attachment portion (552) is coupled to body (510), attachment portion (552) is urged by the resilient material to tightly fit around the exterior of body (510), thereby forming an airtight seal. Alternatively, attachment portion (552) may be sized such that the inner diameter of attachment portion (552) is equal to the diameter of body (510). Further still, if body (510) has an alternative cross-sectional shape, attachment portion (552) may be sized accordingly to provide a seal when coupled to proximal end (514) of body (510). In the present example, attachment portion (552) further comprises a flange recess (556). Flange recess (556) is configured to receive annular flange (516) when body (510) is coupled to seal (550). In yet another configuration, attachment portion (552) may further comprise an outer member, such as an aluminium or stainless steel cylindrical member, to retain the elastomeric or resilient portion therein. Still other configurations for attachment portion (552) will be apparent to one of ordinary skill in view of the teachings herein.

Seal portion (570) is located proximal of attachment portion (552) and is configured to permit passage of needle portion (110) and blade assembly (200) into body (510). In one merely exemplary configuration, seal portion (570) is formed integrally with attachment portion (552), though it should be understood that seal portion (570) may alternatively be a separate component. Indeed, if attachment portion (552) comprises an outer member, seal portion (570) may be separate component that is coupled to attachment portion (570) and retained by the outer member. In the present configuration, seal portion (570) is a simple planar member having an aperture (572) through which needle portion (110) and blade assembly (200) may be inserted. In this configuration, aperture (572) is sized and configured to fit around needle portion (110) such that a seal is substantially formed by seal portion (570) around needle portion (110). Aperture (572) of the present example is an ovular opening that is sized to be smaller than the cross-section of needle portion (110). Alternatively, seal portion (570) may be a simple planar member having a slit or a pair of orthogonal slits. In yet another configuration, seal portion (570) may comprise a duck-bill seal such that the duck bill portion extends proximally from attachment portion (552). As with other components described herein, seal portion (570) may have other configurations as will be apparent to one of ordinary skill in the art in view of the teachings herein.

When needle portion (110) and blade assembly (200) are inserted into needle tip protector (500), lateral aperture (132) is located within body (510) and is substantially sealed therein by seal (550). Accordingly, a user of biopsy device (10) may activate the vacuum pump (50) within holster (30) to test the vacuum produced by vacuum pump (50). In one merely exemplary configuration, probe (20) may arrive to the user preassembled with needle tip protector (500) coupled to the distal end of needle assembly (100). Tubular cutter (60) of this configuration may initially be in a proximal-most position, as shown previously in FIG. 5, such that the fluid within lateral aperture recess (530) is in fluid communication with second lumen portion (142) through lateral aperture (132). Alternatively, tubular cutter (60) may be retracted as part of a diagnostic program, as will be described below.

In the case of a detachable probe (20) having needle tip protector (500) initially coupled thereto, when a user couples probe (20) to holster (30), holster (30) may run a diagnostic program that activates the vacuum pump (50) and uses vacuum sensor (52) to determine whether an appropriate amount of vacuum is generated while needle tip protector (500) is attached. If tubular cutter (60) is not retracted, the diagnostic program may retract tubular cutter (60) prior to activating vacuum pump (50). The diagnostic program may either be automatically activated by the attachment of probe (20) to holster (30) (such as through a sensor detecting the coupling of probe (20) to holster (30) or a switch being activated by the coupling), or the diagnostic program may be manually activated by the user (such as by way of a button or other input). If the vacuum pump (50) fails to create a sufficient vacuum, holster (30) may display a symbol indicating the failure of the diagnostic test and/or a sound generating device may emit an audible sound to indicate the failure of the diagnostic test. Alternatively, if the vacuum pump (50) creates a sufficient vacuum, holster (30) may remain silent or holster (30) may display a symbol indicating the success of the diagnostic test and/or a sound generating device may emit an audible sound to indicate the success of the diagnostic test. If the initial diagnostic test is a success, the user may then remove needle tip protector (500) from needle assembly (100) to use biopsy device (10). While one exemplary use for needle tip protector (500) has been described to test the vacuum created by vacuum pump (50) in holster (30), other suitable uses and configurations for needle tip protector (500) will be apparent to one of ordinary skill in the art in view of the teachings herein. In addition, needle tip protector (500) may be constructed according to at least some of the teachings of U.S. patent application Ser. No. 12/843,088, entitled "Biopsy Device with Detachable Needle Tip Protector," filed Jul. 26, 2010, the disclosure of which is incorporated by reference herein.

IV. Exemplary Vacuum Sensor and Control Module Configuration For Increased Sampling Rate In some situations it may be desirable to reduce the time taken between tissue samples. This may reduces the overall time required for the biopsy device to be inserted within a patient, resulting in less discomfort for the patient, and may also increase the number of patients a physician may see in a given day. Accordingly, one method for accomplishing this includes determining whether a tissue sample has reached the tissue sample holder. Once the tissue sample has been deposited into the tissue sample holder, the biopsy device may reset to the initial position to take another sample.

Referring back to FIGS. 1-3, biopsy device (10) of the present example comprises a motor (70), a plurality of gears (72), vacuum pump (50), vacuum sensor (52), and a control module (1000). In one merely exemplary configuration, motor (50) of biopsy device (10) is mechanically coupled to actuate tubular cutter (60) from the distal-most position to the proximal-most position. In the present configuration, motor (70) contained within holster (30) is mechanically linked to tubular cutter (60) by way of a plurality of gears (72) and/or other components, though it should be understood that these are merely optional. In the configuration shown in FIG. 2 for a detachable probe (20) and holster (30), complementary gears (72) are provided to transfer the rotation provided by motor (70) in holster (30) to tubular cutter (60) in probe (20). Additionally, motor (70) is also operable to activate vacuum pump (50). In one alternative, a second motor (not shown) may be provided to activate vacuum pump (50) instead of using motor (70). Other various configurations for biopsy device (10) may be provided as will be apparent to one of ordinary skill in the art in view of the teachings herein. Indeed, biopsy device (10) may be constructed in accordance with at least some of the teachings of U.S. patent application Ser. No. 12/953,715, entitled "Handheld Biopsy Device with Needle Firing," filed Nov. 24, 2010, the disclosure of which is incorporated by reference herein.

When biopsy device (10) is ready to take a tissue sample, initially tubular cutter (60) is in a distal-most position such that lateral aperture (132) is "closed" as shown in FIG. 4. Thus, when blade assembly (200) and needle portion (110) are inserted into the tissue of a patient, tubular cutter (60) in the distal-most position may substantially prevent tissue from snagging on lateral aperture (132). Once lateral aperture (132) is aligned with the region of tissue that the user desires to sample, tubular cutter (60) may be retracted to the proximal-most position by motor (50). Once tubular cutter (60) is in the proximal-most position, lateral aperture (132) is "opened," as shown in FIG. 5, such that tissue may prolapse into lateral aperture (132). In the present configuration shown, the proximal-most position for tubular cutter (60) is located within the region defined by dwelling portion (138), though it should be understood that proximal-most position for tubular cutter (60) may be located at any point proximal to the proximal edge of lateral aperture (132).

As tubular cutter (60) is retracted, a vacuum may be communicated to first lumen portion (140) and/or second lumen portion (142) from vacuum pump (50) to aid the prolapse of tissue into lateral aperture (132). Alternatively, the vacuum may not be applied by vacuum pump (50) until tubular cutter (60) is in the proximal-most position. In yet another alternative, the vacuum may be selectively applied at any point during the retraction of tubular cutter (60), such as when tubular cutter (60) is retracted 20%-30% of the entire retraction distance. The entire retraction distance may be calculated as the longitudinal displacement between the distal-most position and the proximal-most position. In the present example, the vacuum is communicated by vacuum pump (50) to first lumen portion (140) and into second lumen portion (142) via openings (134) and foremost opening (136), as described above and shown in FIG. 5, thereby providing a lateral vacuum. Thus, when tubular cutter (60) is in the process of retracting, the tissue may be urged to prolapse into second lumen portion (142) through lateral aperture (132) due to the applied vacuum.

Once the tissue is prolapsed within lateral aperture (132), tubular cutter (60) is actuated distally. Tubular cutter (60) may simply translate longitudinally or tubular cutter (60) may both translate and rotate as tubular cutter (60) moves toward the distal-most position. Thus, as tubular cutter (60) is advanced, the prolapsed tissue is severed by tubular cutter (60). A shuttle valve slider may be coupled to tubular cutter (60) to selectively communicate vacuum and/or atmosphere to first lumen portion (160) and/or second lumen portion (162). In particular, the shuttle valve slider may switch the vacuum provided by vacuum pump (50) from first lumen portion (160) to second lumen portion (162) and/or within tubular cutter (60) as tubular cutter (60) is advanced. After tubular cutter (60) has reached the distal-most position, tubular cutter (60) may be configured to rotate in place without further advancing distally. This may be done such that motor (70) continues to operate vacuum pump (50) to provide a vacuum within tubular cutter (60) and second lumen portion (162) to translate the tissue from within second lumen portion (142), through tubular cutter (60), and into tissue sample holder (40). A shuttle valve slider, as described above, may also be actuated such that atmosphere is provided through vent sleeve (180) via transverse openings (182), into first lumen portion (140), and through foremost opening (136) and/or openings (134) to aid the translation of the tissue sample through tubular cutter (60). Once the tissue is stored within tissue sample holder (40) and/or a predetermined period of time has elapsed, as will be described below, biopsy device (10) may reset to an initial state for another tissue sample to be taken.

As described previously, vacuum sensor (52) is configured to sense the vacuum produced by vacuum pump (50). Vacuum sensor (52) is electrically coupled to control module (1000), which may be configured to receive the output signal from vacuum sensor (52) and output control signals to the other components of biopsy device (10). Control module (1000) may be configured in accordance with at least some of the teachings of U.S. patent application Ser. No. 12/953,715, entitled "Handheld Biopsy Device with Needle Firing," filed Nov. 24, 2010, the disclosure of which is incorporated by reference herein. Control module (1000) may comprise hardware and/or software configured to control the various components of biopsy device (10). By way of example only, control module (1000) may comprise RAM memory, flash memory, ROM memory, EPROM memory, EEPROM memory, registers, an ASIC, a programmable processor, and/or any other suitable control module (1000) as will be apparent to one of ordinary skill in the art in view of the teachings herein.

In the present configuration, control module (1000) is partially configured to determine if the tissue severed by tubular cutter (60) has been successfully transferred to tissue sample holder (40) and/or if a predetermined period of time has elapsed. Initially, control module (1000) activates motor (70) coupled to vacuum pump (50) for a predetermined period of time (such as between 0 and 1 second). If vacuum pump (50) produces a sufficient vacuum, the period of time for the tissue sample to travel to the tissue sample holder may be reduced to at or near zero seconds. This may permit more samples to be taken over time.

Figure 11:
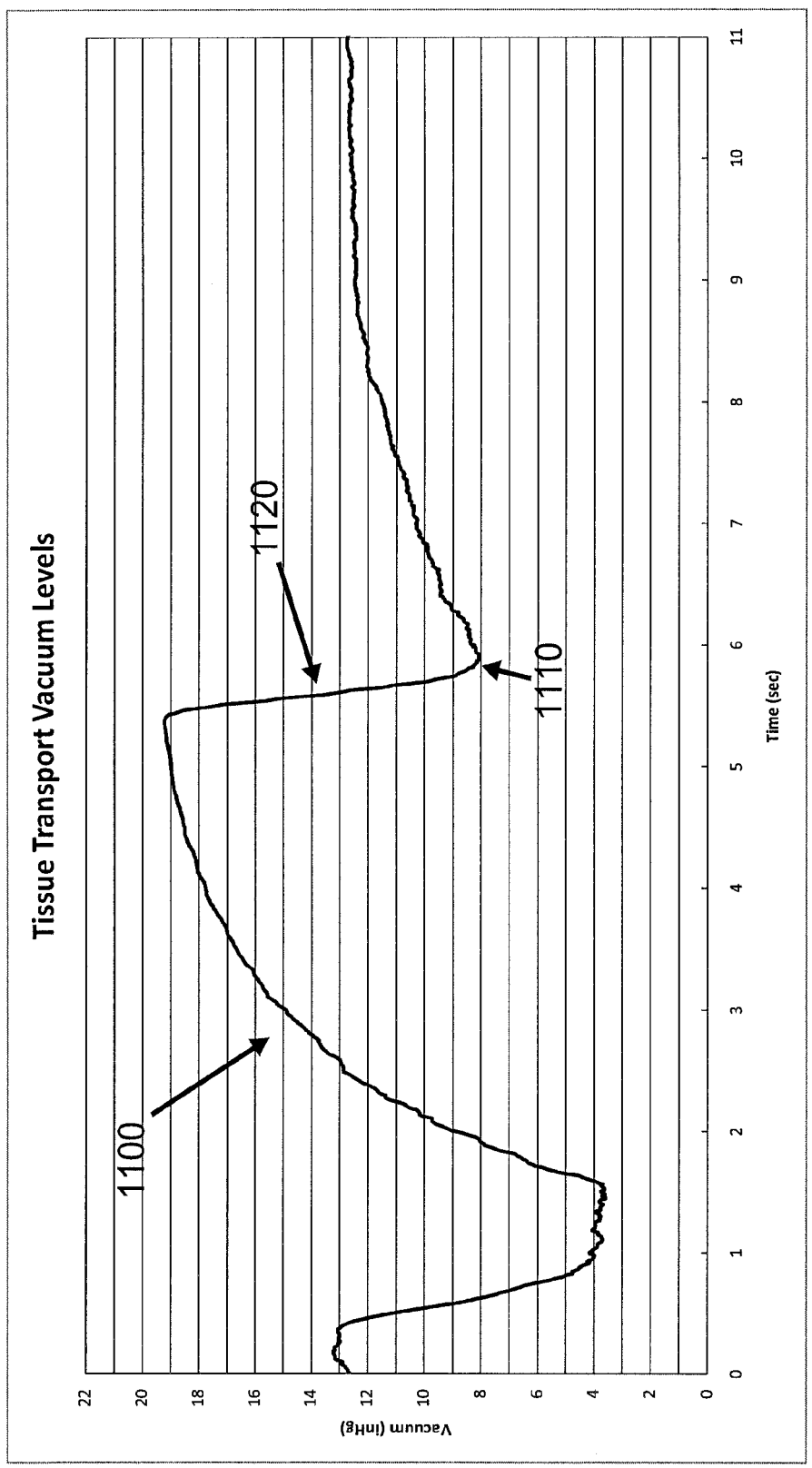
FIG. 11 depicts a graphical representation of an exemplary output signal from a vacuum sensor.

Control module (1000) also receives signal data (1100) from vacuum sensor (52), such as the data shown in FIG. 11. Control module (1000) of the present example may be configured to detect a predetermined vacuum pressure (shown in FIG. 11 as point (1110)) after tubular cutter (60) has been instructed to advance and sever a tissue sample. For example, predetermined vacuum pressure (1110) may be a value in the range of 4 to 10 in Hg, though it should be understood that other values outside of this exemplary range may be chosen based upon the configuration of the device as will be apparent to one of ordinary skill in the art in view of the teachings herein. Predetermined vacuum pressure (1110) may be a static value or predetermined vacuum pressure may be varied according to the speed of motor (70). Predetermined vacuum pressure (1110) may also be a preset factory value or predetermined vacuum pressure (1110) may be determined through testing for various configurations of biopsy device (10) (such variations may include different needle sizes, lengths, sample size selection, and other various variable factors). When control module (1000) detects predetermined vacuum pressure (1110) after tubular cutter (60) advances, control module (1000) is configured to reset biopsy device (10) to the initial state to take another tissue sample. If control module (1000) does not detect predetermined vacuum pressure (1110) and the predetermined period of time has lapsed, then control module (1000) is configured to also reset biopsy device (10) to the initial state or to indicate an error. Thus, if a tissue sample is rapidly transported through second lumen portion (142), through tubular cutter (60), and into tissue sample holder (40), control module (1000) may be configured to reset biopsy device (10) prior to the lapsing of the predetermined period of time described above. Accordingly, it may be possible to take more tissue samples over an equivalent period of time when compared to a biopsy device that merely waits a predetermined period of time, thereby increasing the sampling rate.

Control module (1000) may alternatively be configured to detect a predetermined rate of change in the signal data (1100), represented graphically by the sloped signal data (1120). Sloped signal data (1120) of the present example corresponds to a portion of signal data (1100) output by vacuum sensor (52) that occurs when the severed tissue sample is being transported to tissue sample holder (40). Sloped signal data (1120) may be a preset slope value or it may be determined through prior testing for various configurations of biopsy device (10). One merely exemplary value for sloped signal data (1120) may be −10 in Hg/s. Thus, when control module (1000) detects sloped signal data (1120) that is equal to or a greater negative slope than the set slope value, then control module (1000) is configured to reset biopsy device (10) to the initial state to take another tissue sample. If control module (1000) does not detect sloped signal data (1120) and the predetermined period of time has lapsed, then control module (1000) may be configured to also reset biopsy device (10) to the initial state or to indicate an error. Thus, it may be possible to increase the number of tissue samples over an equivalent period of time in this alternative configuration as well.

In yet a further alternative, a minimum slope value may be set, such as −2 in Hg/s. Control module (1000) may be further configured to adjust the predetermined period of time to accommodate a sloped signal data (1120) value that is between the preset value and the minimum slope value. For instance, if sloped signal data (1120) is −8 in Hg/s, the preset value is −10 in Hg/s, and the minimum value is −2 in Hg/s, control module (1000) may be configured to adjust the predetermined period of time to be longer to permit motor (70) to run vacuum pump (50) longer such that the tissue sample may still be transported to tissue sample holder (40). If the new predetermined period of time lapses, control module (1000) may be configured to then reset biopsy device (10) to the initial state or to indicate an error.

While some merely exemplary methods of adjusting the sampling rate of biopsy device (10) using vacuum sensor (52) and control module (1000) have been described, equally suitable alternative configurations will be apparent to one of ordinary skill in the art in view of the teachings herein.

V. Exemplary Vacuum Pump Muffler

In other situations it may be preferable to keep the noise emitted from biopsy device (10) at a minimum. Providing a quiet or substantially quiet biopsy device (10) may keep a patient calmer during the procedure when compared to a noisy device. Accordingly, reducing the noise output of certain components in biopsy device (10) may achieve this goal. One such component that may produce noise while biopsy device (10) is in use is vacuum pump (50). Accordingly, a muffler may be included with vacuum pump (50) to reduce the noise produced by vacuum pump (50).

Figure 12:
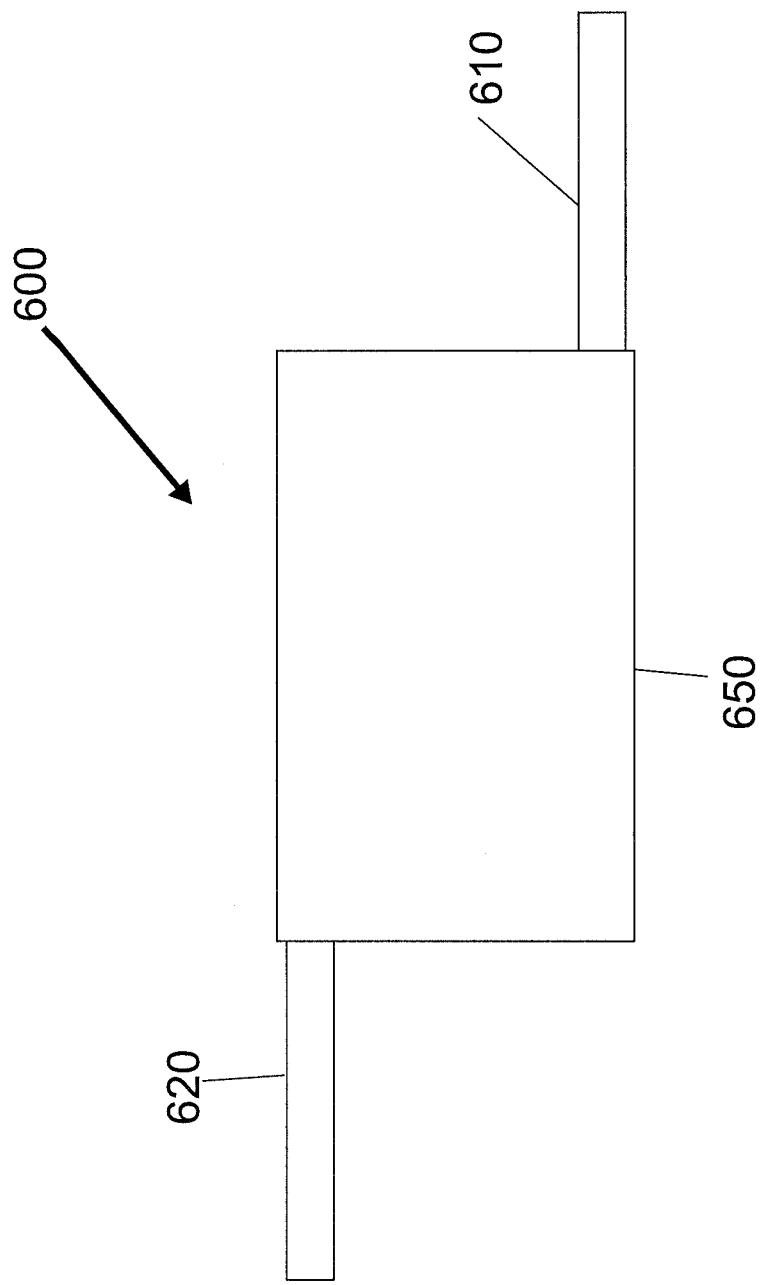
FIG. 12 depicts top view of an exemplary muffler assembly having a muffler, a first outlet tube, and a second outlet tube.

One exemplary configuration is for vacuum pump (50) to be coupled to a muffler assembly (600) shown in FIG. 12. Exemplary muffler assembly (600) comprises a first outlet tube (610) and a second outlet tube (620) coupled to a muffler (650). First outlet tube (610) is coupled to vacuum pump (50) at a first end and coupled to muffler (650) at a second end to provide fluid communication between vacuum pump (50) and muffler (650). First outlet tube (610) may be coupled to muffler (650) using adhesive, a mechanical connection such as a barbed connection on muffler (650), being integrally formed, or by any other suitable means. Second outlet tube (620) is coupled to muffler (620) at a first end and may be coupled to a port on holster (30) at a second end, though it should be understood that the second end of second outlet tube (620) may alternatively be substantially free.

Muffler (650) of the present example comprises a substantially flexible bladder that is inflatable when a fluid, such as air, is pumped into muffler (650). In other configurations, muffler (650) may instead be a rigid structure, such as plastic or metal, and may be a square box, an L-shaped box, an S-shaped tube, or any other suitable shape. Muffler (650) may further comprise baffles, such as rigid plastic fins within a rigid muffler (650) or flexible panels if muffler (650) is a flexible bladder. The baffles may further comprise a plurality of holes to permit a portion of the fluid to flow through each baffle. As shown in FIG. 12, first outlet tube (610) and second outlet tube (620) are coupled on opposing sides of muffler (650) and offset at opposite corners of muffler (650). In one alternative configuration, both tubes (610, 620) may be coupled to muffler (650) on the same side of muffler (650), but at opposite corners. In another configuration, both tubes (610, 620) may be collinearly aligned on opposing sides when coupled to muffler (650). Both tubes (10, 620) may be angularly offset from each other as well. Other equally suitable configurations for first outlet tube (610), second outlet tube (620), and muffler (650) will be apparent to one of ordinary skill in the art in view of the teachings herein.

In the configuration shown in FIG. 12, when muffler assembly (600) is coupled to vacuum pump (50), muffler assembly (600) may reduce the audible noise emitted by vacuum pump (50) by damping the vibrations emitted by vacuum pump (50) using the offset of tubes (610, 620) and by the use of the flexible bladder for muffler (650). In addition, the use of the flexible tubing (610, 620) and flexible muffler (650) may permit muffler assembly (600) to be insertable into a biopsy device having a tight fit because muffler assembly (600) may be maneuvered to any suitable position within the device. Thus, muffler assembly (600) may be provided in a wide variety of biopsy devices, including biopsy device (10), to potentially reduce the noise emitted when the devices are in use. Still other suitable constructions and configurations for muffler assembly (600) may be provided as will be apparent to one of ordinary skill in the art in view of the teachings herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A biopsy device comprising:
 (a) a probe assembly; and
 (b) a needle assembly extending distally from the probe assembly, wherein the needle assembly defines a longitudinal axis, the needle assembly comprising:
  (i) a needle portion having a distal end; and
  (ii) a blade assembly comprising:
   (1) a blade, wherein the blade comprises a first cutting edge and a second cutting edge, wherein the first cutting edge and the second cutting edge are converge to form a point; and
   (2) a multi-member coupling assembly having a proximal end, wherein the multi-member coupling assembly comprises a first coupling member and a second coupling member, wherein the multi-member coupling assembly is configured to couple to the blade on opposite sides of the blade lateral to the longitudinal axis such that a proximal portion of the blade is laterally interposed between the first and second coupling members, and wherein the proximal end of the multi-member coupling assembly is configured to couple to the distal end of the needle portion.

2. The biopsy device of claim 1, wherein the blade comprises a retention channel, and wherein at least one of the first coupling member or the second coupling member comprises a bridge portion configured to be inserted through the retention channel of the blade when the first coupling member and the second coupling member are coupled together.

3. The biopsy device of claim 1, wherein the blade comprises a retention channel having a first region and a second region, wherein the first region is located distally of the second region and the first region is sized such that a portion of the first region is larger than the second region.

4. The biopsy device of claim 3, wherein at least one of the first coupling member or the second coupling member has a first portion configured to be partially insertable through the first region of the retention channel of the blade such that the first portion restricts the longitudinal movement of the blade when the first coupling member and the second coupling member are coupled together.

5. The biopsy device of claim 3, wherein the first coupling member comprises a first portion configured to be partially insertable through the first region of the retention channel of the blade, wherein the first portion comprises a recess at a proximal end of the first portion, wherein the second coupling member comprises a distal protrusion configured to be insertable into the recess when the first coupling member and the second coupling member are coupled together.

6. The biopsy device of claim 5, wherein the second coupling member comprises a bridge portion configured to be partially insertable through the second region of the retention channel, wherein the distal protrusion extends distally from the bridge portion.

7. The biopsy device of claim 1, wherein the first coupling member and the second coupling member collectively form a substantially conical assembly when the first coupling member and the second coupling member are coupled together.

8. The biopsy device of claim 7, wherein the first coupling member comprises a first portion and a second portion, wherein the first portion comprises a conical member, wherein the second portion comprises half a conical member extending from a proximal end of the first portion, wherein the second coupling member is configured to be a substantially complementary half conical member to the second portion of the first coupling member.

9. The biopsy device of claim 1, wherein the blade comprises a substantially flat blade.

10. The biopsy device of claim 1, wherein the blade comprises a first side and a second side, wherein the first side comprises a first planar portion and a first pair of sharpened leading edges intersecting at a tip, wherein the first planar portion of the first side connects to the first pair of sharpened leading edges by a first pair of honed facets, wherein the second side comprises a second planar portion and a second pair of sharpened leading edges intersecting at the tip, and wherein the second planar portion of the second side connects to the second pair of sharpened leading edges by a second pair of honed facets.

11. The biopsy device of claim 1, wherein the blade comprises a retention channel, wherein the multi-member coupling assembly is configured to couple to the blade at least in part by the retention channel.

12. The biopsy device of claim 1, wherein the multi-member coupling assembly comprises a plurality of coupling members.

13. The biopsy device of claim 1, wherein the multi-member coupling assembly further comprises a receiving tube mount, wherein the receiving tube mount is at least partially insertable into the needle portion when the multi-member coupling assembly is coupled to the needle portion.

14. A biopsy blade assembly comprising:
   (a) a blade comprising:
      (i) a first cutting edge,
      (ii) a second cutting edge,
      (iii) a distal end, wherein the distal end terminates in a point formed by the intersection of the first cutting edge and the second cutting edge, and
      (iv) a retention channel passing laterally through the blade from a first exterior blade surface to a second exterior blade surface, wherein the first exterior blade surface and the second exterior blade surface are laterally offset from each other; and
   (b) a multi-member coupling assembly having a proximal end, wherein the multi-member coupling assembly comprises a first coupling member and a second coupling member, wherein the multi-member coupling assembly is configured to couple about the blade such that the first coupling member engages the first exterior blade surface and the second coupling member engages the second exterior blade surface and such that a portion of the multi-member coupling assembly extends laterally through the retention channel of the blade, and wherein the proximal end of the multi-member coupling assembly is configured to couple to a distal end of a biopsy device.

15. The blade assembly of claim 14, wherein the first coupling member and the second coupling member collectively form a substantially conical assembly when the first coupling member and the second coupling member are coupled together.

16. A biopsy device comprising:
   (a) a probe assembly; and
   (b) a needle assembly extending distally from the probe assembly, the needle assembly comprising:
      (i) a needle portion having a distal end; and
      (ii) a blade assembly comprising:
         (1) a multi-member coupling assembly configured to couple to the distal end of the needle portion, wherein the multi-member coupling assembly comprises a first piece defining a first conical surface and a second piece defining a second conical surface, and
         (2) a blade, wherein the blade defines a retention channel, wherein the blade is positioned between the first piece and the second piece of the multi-member coupling assembly such that the first conical surface and the second conical surface are laterally offset relative to the retention channel, wherein the blade extends distally from the multi-member coupling assembly, and wherein the blade comprises a first cutting edge and a second cutting edge, wherein the first cutting edge and the second cutting edge each continuously extend distally until the first cutting edge and the second cutting edge converge to form a point.

\* \* \* \* \*